United States Patent
Nishimura et al.

(10) Patent No.: US 9,205,111 B2
(45) Date of Patent: Dec. 8, 2015

(54) PROCESS FOR PRODUCING ENGINEERED TARGETED T CELL AND MEDICINE

(75) Inventors: Takashi Nishimura, Sapporo (JP); Masaki Yasukawa, Matsuyama (JP)

(73) Assignee: TELLA, INC., Tokyo (JP)

( * ) Notice: Subject to any disclaimer, the term of this patent is extended or adjusted under 35 U.S.C. 154(b) by 225 days.

(21) Appl. No.: 10/583,860

(22) PCT Filed: Dec. 22, 2004

(86) PCT No.: PCT/JP2004/019714
§ 371 (c)(1),
(2), (4) Date: May 21, 2007

(87) PCT Pub. No.: WO2005/061697
PCT Pub. Date: Jul. 7, 2005

(65) Prior Publication Data
US 2008/0019948 A1   Jan. 24, 2008

(30) Foreign Application Priority Data

Dec. 22, 2003   (JP) .............................. 2003-425009

(51) Int. Cl.
| | | |
|---|---|---|
| *C12N 5/00* | (2006.01) |
| *C12N 5/08* | (2006.01) |
| *C12N 15/63* | (2006.01) |
| *C07H 21/04* | (2006.01) |
| *A01N 63/00* | (2006.01) |
| *A61K 39/395* | (2006.01) |
| *A61K 48/00* | (2006.01) |
| *A61K 35/26* | (2015.01) |
| *A61K 39/00* | (2006.01) |
| *C12N 5/0783* | (2010.01) |
| *C12N 15/85* | (2006.01) |
| *C12N 5/16* | (2006.01) |

(52) U.S. Cl.
CPC ............. *A61K 35/26* (2013.01); *A61K 39/0011* (2013.01); *A61K 39/395* (2013.01); *A61K 2039/5156* (2013.01); *C07H 21/04* (2013.01); *C12N 5/0636* (2013.01); *C12N 5/16* (2013.01); *C12N 15/63* (2013.01); *C12N 15/85* (2013.01)

(58) Field of Classification Search
CPC ..... A61K 35/26; A61K 39/395; C12N 15/63; C12N 15/85; C12N 5/0636; C12N 5/16; C07H 21/04
USPC ......... 435/377, 372.3, 455; 424/93.21, 93.71, 424/130.1; 536/23.5
See application file for complete search history.

(56) References Cited

U.S. PATENT DOCUMENTS 6,610,542 B1 *  8/2003  Bell et al. ....................... 435/377
7,323,181 B2 *  1/2008  Gaiger et al. .............. 424/277.1

OTHER PUBLICATIONS

Tsuji et al., Apr. 2003, Cancer Science, vol. 94, No. 4, p. 389-393.*
Ohmi et al., 1999, Cancer Immunology, immunotherapy, vol. 48, p. 456-462.*
Fujio et al., 2000, Journal of Immunology, vol. 165, p. 528-532.*
Kessels et al., 2001, Nature Immunology, vol. 2, No. 10, p. 957-961.*
Morgan et al., Sep. 2003, The Journal of Immunology, vol. 171, p. 3287-3295.*
Clay et al., 1999, The Journal of Immunology, vol. 163, p. 507-513.*
Baldwin et al., 2006, US 20060210556 A1, effective filed, Apr. 29, 2003.*
Maeda et al., 2004, US 20040151723 A1, effective filed, Jun. 8, 2001.*
Gruenberg, Michael L., 2002, US 20020182730 A1.*
Grimm et al. Journal of Experimental Medicine. vol. 155, Jun. 1982 p. 1823-1841.
Taniguchi et al. Mar. 1983. Nature, vol. 302: p. 305-310.
Rosenberg et al. Dec. 1985. New England Journal of Medicine, vol. 313 No. 23, p. 1485-1492.
Ochoa et al. 1987. Journal of Immunology. vol. 138: No. 8. p. 2728-2733.
Mosmann et al. Apr. 1986. Journal of Immunology. vol. 136, No. 7 : p. 2348-2357.
Maggi et al. Apr. 1992, Journal of Immunology, vol. 148: No. 7, p. 2142-2147.
Seder et al. Nov. 1993. Proc. Natl. Acad. Sci. USA. vol. 90, p. 10188-10192.
Hsieh et al. Jul. 1992. Proc. Natl. Acad. Sci. USA, vol. 89, p. 6065-6069.
Mosmann et al. Mar. 1996. Immunology Today, vol. 17: No. 3, p. 138-146.
Morgan et al. 2003. Journal of Immunology., vol. 171, p. 3287-3295.
Sato et al., Igaku no ayumi, 2000, vol. 195 No. 1, p. 3-8.
Nishimura, Cancer Treatment and Host 2000 vol. 12 No. 4, p. 363-373.
Nishimura, Clinical Immunology 2002 vol. 38 No. 4, p. 363-369.
Nishimura, Igaku no ayumi 2002 vol. 200 No. 6, p. 481-486.
Kikuchi, Tumor immunity and immunotherapy 1997, p. 525-528.
Kinebuchi et al., Hematology & Oncology 1999, vol. 38 No. 1 p. 22-29.

(Continued)

*Primary Examiner* — Shin Lin Chen
(74) *Attorney, Agent, or Firm* — Birch, Stewart, Kolasch & Birch, LLP

(57) ABSTRACT

A novel process for preparing tumor-specific T cells is disclosed. According to the invention, antitumor-active, tumor-specific T cells are prepared by transducing a TCR gene from a tumor-specific CTL into antitumor-active T cells that have been nonspecifically activated, thus enabling tumor-specific cellular immunotherapy to be carried out from even small amounts of blood. MHC class I-restricted, tumor-specific Th cells are obtained by the method, allowing for the production of cells that react with tumor cells expressing an MHC class I molecule and show a helper activity and an antitumor activity.

9 Claims, 3 Drawing Sheets

(56) References Cited

OTHER PUBLICATIONS

Jeanin P. et al., Journal of Immunology (1996), vol. 156, p. 3159-3165.

Tsuji et al., Cancer Sci. Apr. 2003, vol. 94 No. 4, p. 389-393.

Tamura et al., Grants-in-Aid for Scientific Research, Ministry of Education, Culture, Sports, Science and Technology, pp. 525-528 (1997).

Mosmann et al., Cancer Therapy & Host, vol. 12, No. 4, pp. 363-373, (2000).

* cited by examiner

PROCESS FOR PRODUCING ENGINEERED TARGETED T CELL AND MEDICINE

TECHNICAL FIELD

The present invention relates to a process of preparing an activated T cell-based medicine that can specifically damage tumor cells, comprising transducing a gene for a T cell receptor that specifically recognizes a tumor antigen into nonspecifically activated Th cells or Th1 cells and Tc1 cells that have antitumor activity. The present invention also relates to the application of the activated T cell-based medicine.

BACKGROUND ART

As used herein, cancer refers to a malignant neoplasm, and cancer and tumor are regarded as synonymous.

Lymphokine-activated killer (LAK) cells exhibiting a broad antitumor activity against natural killer (NK) cell-resistant tumors can be induced by separating mononuclear cells from the peripheral blood and culturing them in the presence of interleukin-2 (IL-2) (see, for example, Grimm et al., 1982, *J. Exp. Med.,* 155: 1823-1841). Subsequently, IL-2 has become available in large amounts as a consequence of genetic recombination technology (see, for example, Taniguchi et al., 1983, *Nature,* 302: 305-310), and adoptive immunotherapy using LAK cells against tumors was clinically applied and was shown to be effective (see, for example, Rosenberg et al., 1985, *New Engl. J. Med.,* 313: 1485-1492).

It has also become possible to culture cells in the presence of anti-CD3 monoclonal antibody (MoAb) and IL-2 to obtain a large amount of cells exhibiting LAK activity from mononuclear cells derived from small amounts of peripheral blood (see, for example, Ochoa et al., 1987, *J. Immunol.,* 138: 2728-2733).

Peripheral T lymphocytes express a CD3 molecule together with a T cell receptor (TCR) on the cell surface and are classified into helper T (Th) cells and cytotoxic T cells (CTL) depending on whether the CD4 or CD8 molecule is expressed.

Cells having a targeted cell surface antigen can be enriched or removed through the use of magnetic beads and MoAb against molecules such as CD4 molecule or CD8 molecule expressed on the cell surface (see, for example, Japanese Patent 2,530,966).

Th cells are classified into Th1 cells, which produce cytokines such as interferon-γ (IFN-γ) and IL-2, and Th2 cells, which produce cytokines such as IL-4 and IL-10 (see, for example, Mosmann et al., 1986, *J. Immunol.,* 136: 2348-2357). Th1 cells function as an effector of cellular immunity, while Th2 cells are responsible for regulating humoral immunity. In addition, IFN-γ produced by Th1 cells inhibits Th2 cells, while IL-4 produced by Th2 cells inhibits Th1 cells (see, for example, Maggi et al., 1992, *J. Immunol.,* 148: 2142-2147).

During the initial phase of Th cell activation, differentiation of Th1 cells is induced by the presence of IL-12 (see, for example, Seder et al., 1993, *Proc. Natl. Acad. Sci. USA,* 90: 10188-10192), while Th2 cell differentiation is induced by the presence of IL-4 (see, for example, Hsieh et al., 1992, *Proc. Natl. Acad. Sci. USA,* 89: 6065-6069).

CTLs, on the other hand, are classified into Tc1 cells and Tc2 cells based on cytokine production patterns that are the same as for the Th1 and Th2 cells. Tc1 cells exhibit a strong cytotoxicity, while Tc2 cells are responsible for immunosuppressive function. Differentiation into Tc1 cells or Tc2 cells is regulated by the presence of IL-12 or IL-4 (see, for example, Mosmann et al., 1996, *Immunology Today,* 17: 138-146).

T cells bind to a target cell, such as an antigen presenting cell (APC), by recognizing an MHC molecule/peptide antigen complex through the TCR. It is reported that CTLs bind to only an MHC class I molecule/peptide antigen complex (MHC class I restriction), while Th cells can bind only to an MHC class II molecule/peptide antigen complex (MHC class II restriction).

In addition, MHC class I molecules are expressed on almost all nucleated cells, while MHC class II molecules are expressed only on a limited number of cells. As a consequence, Th cells has the ability to bind to cells that express MHC class II molecules, for example, dendritic cells, B cells, and activated T cells, but are unable to directly bind to other cells, for example, tumor cells or infected cells.

However, it has been shown that MHC class II-restricted $CD4^+CD8^-$ T cells genetically engineered to bear a TCR gene originating from an MHC class I-restricted CTL can be activated by reacting with an APC pulsed with the corresponding antigen in a CD8-independent manner, suggesting that the T cells express a TCR capable of binding to the corresponding antigen. In addition, a tumor can be specifically damaged by transducing a TCR gene originating in a tumor antigen-specific CTL into peripheral blood lymphocytes that have a non-specific antitumor activity (see, for example, Morgan et al., 2003, *J. Immunol.,* 171: 3287-3295).

In order to induce tumor-specific T cells in vitro, cancer tissue must be surgically obtained from the patient. Also it has recently become possible to induce tumor-specific T cells using tumor peptide antigen, but this procedure can be adapted only to patients with a limited type of MHC.

Moreover, substantial time and effort is required to induce tumor-specific T cells, and a large amount of blood is required to obtain APCs used for induction. These circumstances have made it difficult to obtain tumor-specific T cells in a quantity required for cell therapy.

An object of the present invention, therefore, is to provide a novel process for preparing tumor-specific T cells, particularly Th cells or both Th1 cells and Tc1 cells.

Furthermore, MHC class I molecules are expressed in almost all nucleated cells, while MHC class II molecules are expressed only in some cells including activated cells, and as a consequence helper T cells are unable to directly bind to all cells.

Another object of the present invention, therefore, is to provide a novel process for preparing tumor-specific helper T cells, particularly TH1 cells, that can bind to MHC class I molecules.

DISCLOSURE OF THE INVENTION

The present inventors have discovered that a tumor-specific TCR gene can be transduced into Tc1 cells having a nonspecific antitumor activity to form T cells that can specifically damage tumor cells. The present inventors have further discovered that a TCR gene obtained from an MHC class I-restricted antigen-specific CTL can be transduced into non-specifically activated MHC class II-restricted Th1 cells to form T cells that can react with MHC class I molecule/peptide antigen complexes and exhibit a helper activity as well as an antitumor activity.

The present invention provides a process of preparing cells for cell therapy, comprising the steps of inducing Th cells that have a nonspecific antitumor activity; and imparting antigen specificity to the Th cells. The step of imparting antigen specificity to the T cells is preferably carried out by transducing a gene for a TCR that recognizes a cancer-associated antigen. The step of imparting antigen specificity to the Th cells is also preferably carried out by transducing a gene for a class I-restricted TCR that recognizes a cancer-associated antigen. The step of imparting antigen specificity to the Th cells is also preferably carried out by transducing a gene for a class II-restricted TCR that recognizes a cancer-associated antigen.

The present invention also provides cells for cell therapy, that are prepared by a process comprising the steps of inducing Th cells that have a nonspecific antitumor activity; and imparting antigen specificity to the Th cells. In another embodiment, the present invention provides a method for preventing or treating tumor, comprising the steps of isolating leukocytes from a patient; inducing from the leukocytes Th cells that have a nonspecific antitumor activity; imparting antigen specificity to the Th cells; and administering to the patient the Th cells to which antigen specificity has been imparted.

In another embodiment, the present invention provides a process of preparing cells for cell therapy, comprising the steps of inducing Th1 cells and Tc1 cells that have a nonspecific antitumor activity; and imparting antigen specificity to the Th1 cells and Tc1 cells. The step of imparting antigen specificity to the T cells is preferably carried out by transducing a gene for a TCR that recognizes a cancer-associated antigen. The step of imparting antigen specificity to the Th1 cells and Tc1 cells is also preferably carried out by transducing a gene for a class I-restricted TCR that recognizes a cancer-associated antigen. The step of imparting antigen specificity to the Th1 cells and Tc1 cells is also preferably carried out by transducing a gene for a class II-restricted TCR that recognizes a cancer-associated antigen.

The present invention also provides cells for cell therapy, that are prepared by a process comprising the steps of inducing Th1 cells and Tc1 cells that have a nonspecific antitumor activity; and imparting antigen specificity to the Th1 cells and Tc1 cells. In another embodiment, the present invention provides a method for preventing or treating tumor, comprising the steps of isolating leukocytes from a patient; inducing from the leukocytes Th1 cells and Tc1 cells that have a nonspecific antitumor activity; imparting antigen specificity to the Th1 cells and Tc1 cells; and administering to the patient the Th1 cells and Tc1 cells to which antigen specificity has been imparted.

In the process according to the present invention, the cancer-associated antigen is preferably selected from the group consisting of WT1, CEA, AFP, CA19-9, CA125, PSA, CA72-4, SCC, MK-1, MUC-1, p53, HER2, G250, gp-100, MAGE, BAGE, SART, MART, MYCN, BCR-ABL, TRP, LAGE, GAGE, and NY-ESO1.

In another embodiment, the step of inducing Th cells having a nonspecific antitumor activity in the process according to the present invention is carried out by culturing a T cell-containing material isolated from, for example, the peripheral blood of a patient, in the presence of anti-CD3 antibody and IL-2.

In another embodiment, the step of inducing Th1 cells and Tc1 cells having a nonspecific antitumor activity in the process according to the present invention is carried out by culturing a T cell-containing material isolated from, for example, the peripheral blood of a patient, in the presence of anti-CD3 antibody, IL-2, and IL-12; preferably in the presence of anti-CD3 antibody, IL-2, IL-12, and anti-IL-4 antibody; and more preferably in the presence of anti-CD3 antibody, IL-2, IL-12, anti-IL-4 antibody, and IFN-γ.

In another embodiment, the process according to the present invention further comprises a step of separating the Th1 cells and Tc1 cells to which antigen specificity has been imparted. The step of separating the Th1 cells and Tc1 cells to which antigen specificity has been imparted is preferably carried out by using antibody-bearing magnetic beads.

In another embodiment, the process according to the present invention further comprises a step in which the separated Th1 cells and Tc1 cells are mixed in any proportion.

DETAILED DESCRIPTION OF THE INVENTION

Figure 1:
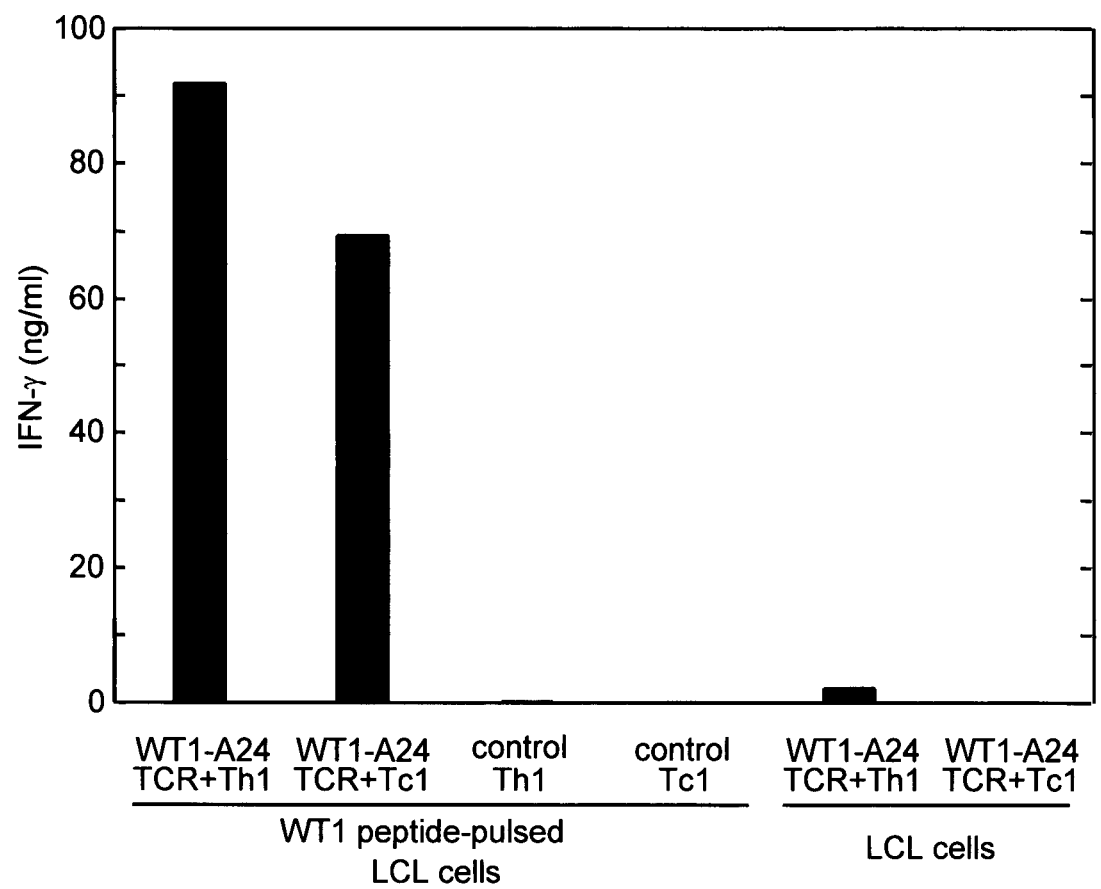
FIG. 1 shows a comparison of the IFN-γ production capacity of WT1-A24TCR+Th1 cells and WT1-A24TCR+Tc1 cells when co-cultured with WT1 peptide-pulsed LCL cells or non-peptide-pulsed LCL cells.

The process according to the present invention for preparing cells for cell therapy comprises the steps of inducing Th cells having a nonspecific antitumor activity; and imparting antigen specificity to the Th cells.

The Th cells having a nonspecific antitumor activity can be induced as described below. Mononuclear cells are isolated from human peripheral blood by, for example, specific gravity centrifugation, and are cultured in a medium (AIM-V (Invitrogen), human AB blood serum or serum that is the same blood type as the cultured cells and preferably autologous serum at 0.1 to 30%, preferably at 5 to 10%) in the presence of anti-CD3 antibody and IL-2. The final concentration of IL-2 is 10 to 2000 IU/mL, and preferably 50 to 500 IU/mL. Antigen-nonspecifically activated Th cells can be induced in this manner.

In another embodiment, the process according to the present invention for preparing cells for cell therapy comprises the steps of inducing Th1 and Tc1 cells having a nonspecific antitumor activity; and imparting antigen specificity to these Th1 cells and Tc1 cells.

The Th1 cells and Tc1 cells having a nonspecific antitumor activity can be induced as follows. Mononuclear cells are isolated from human peripheral blood by, for example, specific gravity centrifugation, and are cultured in a medium (AIM-V (Invitrogen), with human blood serum: AB blood serum or serum that is the same blood type as the cultured cells, and preferably autologous serum, at 0.1 to 30%, preferably at 5 to 10%) in the presence of anti-CD3 antibody, IL-2, and IL-12, preferably in the presence of anti-CD3 antibody, IL-2, IL-12, and anti-IL-4 antibody, and more preferably in the presence of anti-CD3 antibody, IL-2, IL-12, anti-IL-4 antibody, and IFN-γ. The preferred concentration of each cytokine, in a final concentrations of 10 to 2000 IU/mL and preferably 50 to 500 IU/mL of IL-2, 1 to 1000 IU/mL and preferably 10 to 200 IU/mL of IL-12, 1 to 500 ng/mL and preferably 5 to 100 ng/mL of IFN-γ, and 0.1 to 100 μg/mL and preferably 0.5 to 10 μg/mL of anti-IL-4 antibody. Antigen-nonspecifically activated Th1 cells and Tc1 cells can be induced in this manner.

Next, antigen specificity for tumor cells is imparted to the Th cells or Th1 cells and Tc1 cells obtained as described above which have a nonspecific antitumor activity. The step of imparting antigen specificity to the Th cells or Th1 cells and Tc1 cells is carried out by transducing a gene for a TCR that recognizes a cancer-associated antigen to allow for expression of the TCR on the surface of those Th cells or Th1 cells or Tc1 cells. The TCR may be a class I-restricted TCR or a class II-restricted TCR.

The TCR gene can be isolated from a tumor-specific human CTL clone. The tumor-specific CTL clone may be cloned by limit dilution of isolated human T cells or may be induced by in vitro cultivation of isolated human CTLs in the presence of an antigen. TCR gene may be readily cloned by the 5' RACE procedure using primers corresponding to the sequences specific to the TCR α-chain gene and the TCR β-chain gene.

The TCR gene can be transduced into the T cells using any of various viral vectors. Such vectors may include, for example, lentivirus vectors, retrovirus vectors, adenovirus vectors, adeno-associated virus vectors, Sendai virus vectors, and liposomes. The vector comprises, inter alia, a promoter region, initiation codon, stop codon, and terminator region, which are arranged in an order that enables expression of the TCR gene in the T cells. The viral vector incorporating the TCR gene can be transduced into the antigen-nonspecifically activated T cells utilizing, for example, a suitable packaging plasmid or helper plasmid. Proceeding in this manner provides Th cells or Th1 cells and Tc1 cells to which specificity for tumor cells has been imparted.

In a preferred embodiment of the present invention, a TCR gene from a tumor-specific CTL may be transduced into MHC class II-restricted Th cells as the antigen-nonspecifically activated T cells to obtain Th cells that can directly bind to tumor cells through the expression of a class I-restricted TCR. Such a Th cell is very useful for application in the treatment of cancer, because it has both an antitumor activity and a helper activity. The Th cells are particularly preferably Th1 cells.

In addition, Th cells to which antigen specificity has been imparted may be purified from the activated T cell population obtained as described above. This process can be carried out by isolating antigen-specific CD4 positive cells using magnetic beads bearing anti-CD4 antibody.

Th1 cells and Tc1 cells to which antigen specificity has been imparted may also be separated from the activated T cell population obtained as described above. This process can be carried out by isolating antigen-specific CD4 positive cells or antigen-specific CD8 positive cells using magnetic beads bearing anti-CD4 antibody or anti-CD8 antibody. The Th1 cells and Tc1 cells isolated in this manner can be mixed in any proportion so as to obtain an optimal effect in cancer treatment.

The Th cells or Th1 cells and Tc1 cells having antigen specificity obtained by the process according to the present invention can be evaluated for their antigen specificity as follows. Human peripheral blood mononuclear cells of known HLA are transformed with EB virus to obtain a lymphoblastoid cell line (LCL). The cells are peptide-pulsed by adding to the culture medium a corresponding HLA-restricted peptide derived from the target antigen. This process yields LCL cells in which the corresponding HLA/peptide antigen complex is expressed on the cell surface. The Th cells or Th1 cells or Tc1 cells having antigen specificity obtained by the process according to the present invention are then co-cultured with mitomycin C-inactivated, peptide-pulsed LCL cells or with non-peptide-pulsed LCL cells as a control. The antigen specificity can then be determined by measuring and comparing the amount of IFN-γ or IL-2 in the culture supernatants.

The Th cells or Th1 cells or Tc1 cells having antigen specificity obtained by the process according to the present invention can be evaluated for their antitumor activity by bringing the T cells into contact with $^{51}$Cr-labeled, peptide-pulsed LCL cells for a predetermined period of time, and measuring the amount of $^{51}$Cr released from the cells.

The content of all patents and reference documents expressly cited in the specification of this application are hereby incorporated by reference in its entirety. In addition, the content of the specification and drawings of Japanese Patent Application 2003-425009, which is the basis for the priority claim of this application, are hereby incorporated by reference in its entirety.

EXAMPLES

The present invention is described in greater detail by the examples provided below, but these examples are not intended to limit the scope of the present invention.

Example 1

The TCR α-chain gene and TCR β-chain gene were isolated by the 5' RACE procedure from TAK-1, a CTL clone derived from an HLA-A24 positive healthy donor and specific for tumors having the WT1 tumor antigen, and then the sequence of the genes was determined.

The WT1-specific TCR α-chain gene and TCR β-chain gene originating from the CTL of an HLA-A24 positive healthy donor were incorporated into the lentivirus-vector CSII and introduced into *E. coli* strain DH10B. The amplified vector was purified by a CaCl$_2$ centrifugation method.

The CSII lentivirus vector incorporating the WT1-specific TCR α-chain gene and TCR β-chain gene originating from the CTL of an HLA-A24 positive healthy donor was added to a culture of 293T cells along with the packaging plasmid pMDLg/pRRE, the Rev expression plasmid pRVS-Rev, and the VSV-G plasmid pMD.G, and continued incubation. After treatment with forskolin, a culture supernatant was collected that contained large amounts of lentivirus vector incorporating the TCR α-chain gene and TCR β-chain gene.

Example 2

Nonspecific Activation of T Cells

Anti-CD3 antibody-coated plates were prepared in advance by immobilizing anti-CD3 antibody on culture plates. Mononuclear cells isolated from peripheral blood by specific gravity centrifugation method were cultured under type 1 culture conditions in the presence of 100 IU/mL of IL-2, 50 IU/mL of IL-12, 10 ng/mL of IFN-γ, and 2 μg/mL of anti-IL-4 antibody (type 1 cytokines).

Example 3

Preparation of TCR Gene-Transduced T Cells

The lentivirus vector-containing culture supernatant obtained in Example 1 and type 1 cytokines were added to mononuclear cells that had been cultured for 2 days under type 1 culture conditions and cultivation was continued. After 24 hours, the lentivirus vector-containing culture supernatant and type 1 cytokines were added again and cultivation was continued, whereby the WT1-specific TCR α-chain gene and TCR β-chain gene originating from the CTL of an HLA-A24 positive healthy donor were transduced into non-specifically activated T cells.

The activated T cells transduced with the WT1-specific TCR α-chain gene and TCR β-chain gene originating from the CTL of an HLA-A24 positive healthy donor was expanded for additional 10 days.

From the T cells which had been nonspecifically activated under type 1 culture conditions and transduced with the WT1-specific TCR α-chain gene and TCR β-chain gene originating from the CTL of an HLA-A24 positive healthy donor, CD4 positive T cells (Th1 cells) and CD8 positive T cells (Tc1 cells) were isolated using commercially available MACS MicroBeads CD4 and MACS MicroBeads CD8 (Miltenyi Biotec), respectively.

Example 4

Evaluation of the Antitumor Activity of the TCR Gene-Transduced T Cells

HLA-A24 is the most frequently occurring human MHC class I antigen in the Japanese population. An HLA-A24 positive lymphoblastoid cell line (LCL) obtained by EB viral transformation of peripheral blood mononuclear cells from an HLA-A24 positive healthy donor were used for the hypothetical tumor cell population. HLA-A24-restricted peptide from WT1 protein was added at a concentration of 10 μg/mL for 16 hours (peptide-pulse), then unreacted peptide was washed off. This procedure yields LCL cells expressing an HLA-A24/WT1 peptide complex on the cell surface.

The Th1 cells (WT1-A24TCR+Th1 cells) or Tc1 cells (WT1-A24TCR+Tc1 cells) purified in Example 3 were co-cultured for 24 hours with either the WT1 peptide-pulsed LCL cells or nonpulsed LCL cells, both of which had been inactivated by treatment with mitomycin C. Then the level of IFN-γ and IL-2 in the culture supernatant was measured.

IFN-γ production was observed for both WT1-A24TCR+ Th1 cells and WT1-A24TCR+Tc1 cells co-cultured with WT1 peptide-pulsed LCL cells, but not for those co-cultured with non-peptide-pulsed LCL cells (FIG. 1).

IL-2 production was observed for the WT1-A24TCR+Th1 cells and WT1-A24TCR+Tc1 cells co-cultured with WT1 peptide-pulsed LCL cells, but the production level of the WT1-A24TCR+Tc1 cells was lower than the Th1 cells. IL-2 production was not detected for either the WT1-A24TCR+ Th1 cells or the WT1-A24TCR+Tc1 cells co-cultured with non-peptide-pulsed LCL cells (FIG. 2).

Figure 2:
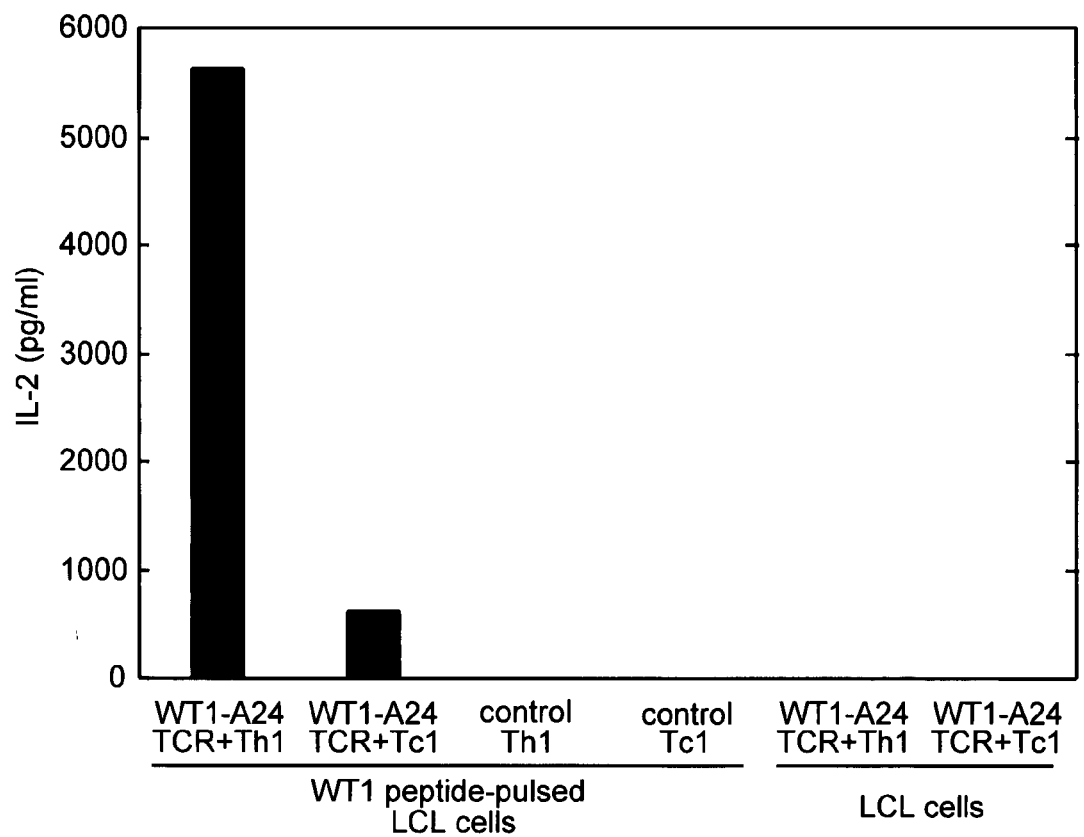
FIG. 2 shows a comparison of the IL-2 production capacity of WT1-A24TCR+Th1 cells and WT1-A24TCR+Tc1 cells co-cultured with WT1 peptide-pulsed LCL cells or non-peptide-pulsed LCL cells.

With regard to the control Th1 cells and control Tc1 cells, which were comparative controls that were not transduced with the WT1-specific TCR gene, the production of IFN-γ or IL-2 was not detected when co-cultured with WT1 peptide-pulsed LCL cells (FIGS. 1 and 2).

The cytotoxicity of the purified WT1-A24TCR+Th1 cells or WT1-A24TCR+Tc1 cells was measured in a 4-hour $^{51}$Cr release assay using $^{51}$Cr-labeled, WT1 peptide-pulsed LCL cells as the target cells. The cytotoxicity of control Th1 cells and control Tc1 cells, which were not transduced with the WT1-specific TCR gene, was also measured as a comparative control.

Figure 3:
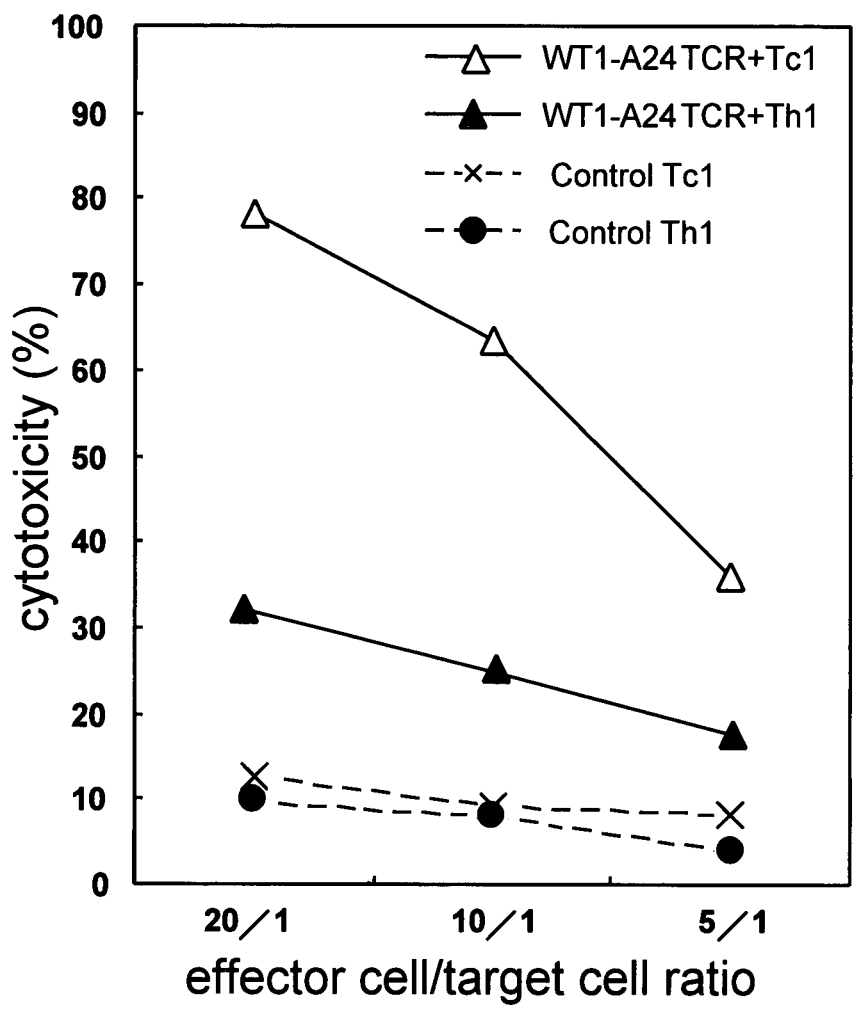
FIG. 3 shows the cytotoxicity of WT1-A24TCR+Th1 and WT1-A24TCR+Tc1 cells against peptide-pulsed LCL cells.

The WT1-A24TCR+Th1 cells exhibited cytotoxicity, while the control Th1 cells exhibit no cytotoxicity. In addition, the WT1-A24TCR+Tc1 cells exhibited a much stronger cytotoxicity than did the WT1-A24TCR+Th1 cells, while cytotoxicity was not shown in the control Tc1 cells (FIG. 3).

These results demonstrated that the Tc1 cells having a nonspecific antitumor activity can be genetically engineered by transducing a tumor-specific TCR gene to obtain cells capable of specifically damaging tumor cells. In addition, it was shown that nonspecifically activated MHC class II-restricted Th1 cells can be genetically engineered by transducing a TCR gene obtained from an MHC class I-restricted antigen-specific CTL to obtain cells capable of reacting with an MHC class I molecule/peptide antigen complex and having both helper activity and antitumor activity.

INDUSTRIAL APPLICABILITY

The activated T cell medicine according to the present invention can specifically damage tumor cells and thus is useful in the treatment of cancer.

| Keys to the figures. |
|---|
| FIG. 1<br>upper line in x-axis label, left to right:<br>                      control        control<br>                      Th1             Tc1<br>lower line in x-axis label, left to right:<br>    WT1 peptide-pulsed               LCL cells<br>        LCL cells<br>FIG. 2<br>upper line in x-axis label, left to right:<br>                      control        control<br>                      Th1            Tc1<br>lower line in x-axis label, left to right:<br>    WT1 peptide-pulsed               LCL cells<br>        LCL cells<br>FIG. 3<br>y-axis: cytotoxicity (%)<br>x-axis: effector cell/target cell ratio | x - label: control Tc1
• - label: control Th1

The invention claimed is:

1. A process of preparing a cell population which is dominant of Th1 cells having cancer-associated antigen specificity and produce IL-2 for cell therapy, which comprises the steps of;
   a) incubating mononuclear cells in a culture medium, wherein the culture medium comprises a factor affecting differentiation of mononuclear cells into Th1 cells, whereby the mononuclear cells are differentiated into Th1 cells; and
   b) transforming the incubated mononuclear cells of a) with an MHC class I-restricted T cell receptor gene that recognizes a cancer-associated antigen, followed by culturing the cells,
   whereby Th1 cells which have cancer-associated antigen specificity and produce IL-2 are dominantly activated or proliferated.

2. The process according to claim 1, wherein the culture medium of step a) and/or step b) further comprises IL-2 and/or anti-CD3 antibody.

3. The process according to claim 2, wherein the factor affecting Th1 differentiation is selected from one or more of the group consisting of: IFN-gamma, IL-12, and anti-IL-4 antibody.

4. The process according to claim 2, wherein the cancer-associated antigen is selected from the group consisting of Wilms' Tumor 1 (WT1), Carcinoembryonic antigen (CEA), Alpha-fetoprotein (AFP), carbohydrate antigen 19-9 (CA 19-9), cancer antigen 125 (CA125), Prostate-specific antigen (PSA), carbohydrate antigen 72-4 (CA72-4), Squamous cell carcinoma antigen (SCC), epithelial cell adhesion molecule (MK-1), mucin 1 (MUC-1), p53 tumor suppressor (p53), Tyrosine kinase-type cell surface receptor HER2 (HER2), Carbonic anhydrase 9 precursor (G250), Melanocyte lineage-specific antigen GP100 (gp100), melanoma antigen family (MAGE), B melanoma antigen 1 precursor (BAGE), squamous cell carcinoma antigen recognized by T cells (SART), Melanoma antigen recognized by T cells (MART), v-myc avian myelocytomatosis viral oncogene neuroblastoma derived homolog (MYCN), Breakpoint cluster region (BCR)-Abelson murine leukemia viral oncogene homolog 1 (ABL) fusion protein (BCR-ABL), tyrosinase-related protein (TRP), Autoimmunogenic cancer/testis antigen (LAGE), and G antigen family (GAGE).

5. The process according to claim 1, wherein the factor affecting Th1 differentiation is selected from one or more of the group consisting of: IFN-gamma, IL-12, and anti-IL-4 antibody.

6. The process according to claim 5, wherein the cancer-associated antigen is selected from the group consisting of Wilms' Tumor 1 (WT1), Carcinoembryonic antigen (CEA), Alpha-fetoprotein (AFP), carbohydrate antigen 19-9 (CA 19-9), cancer antigen 125 (CA125), Prostate-specific antigen (PSA), carbohydrate antigen 72-4 (CA72-4), Squamous cell carcinoma antigen (SCC), epithelial cell adhesion molecule (MK-1), mucin 1 (MUC-1), p53 tumor suppressor (p53), Tyrosine kinase-type cell surface receptor HER2 (HER2), Carbonic anhydrase 9 precursor (G250), Melanocyte lineage-specific antigen GP100 (gp100), melanoma antigen family (MAGE), B melanoma antigen 1 precursor (BAGE), squamous cell carcinoma antigen recognized by T cells (SART), Melanoma antigen recognized by T cells (MART), v-myc avian myelocytomatosis viral oncogene neuroblastoma derived homolog (MYCN), Breakpoint cluster region (BCR)-Abelson murine leukemia viral oncogene homolog 1(ABL) fusion protein (BCR-ABL), tyrosinase-related protein (TRP), Autoimmunogenic cancer/testis antigen (LAGE), and G antigen family (GAGE).

7. The process according to claim 1, wherein the cancer-associated antigen is selected from the group consisting of Wilms' Tumor 1 (WT1), Carcinoembryonic antigen (CEA), Alpha-fetoprotein (AFP), carbohydrate antigen 19-9 (CA 19-9), cancer antigen 125 (CA125), Prostate-specific antigen (PSA), carbohydrate antigen 72-4 (CA72-4), Squamous cell carcinoma antigen (SCC), epithelial cell adhesion molecule (MK-1), mucin 1 (MUC-1), p53 tumor suppressor (p53), Tyrosine kinase-type cell surface receptor HER2 (HER2), Carbonic anhydrase 9 precursor (G250), Melanocyte lineage-specific antigen GP100 (gp100), melanoma antigen family (MAGE), B melanoma antigen 1 precursor (BAGE), squamous cell carcinoma antigen recognized by T cells (SART), Melanoma antigen recognized by T cells (MART), v-myc avian myelocytomatosis viral oncogene neuroblastoma derived homolog (MYCN), Breakpoint cluster region (BCR)-Abelson murine leukemia viral oncogene homolog 1(ABL) fusion protein (BCR-ABL), tyrosinase-related protein (TRP), Autoimmunogenic cancer/testis antigen (LAGE), and G antigen family (GAGE).

8. The process according to claim 1, wherein the process further comprises:
   c) purifying the Th1 cells which have cancer-associated antigen specificity and produces IL-2 by contacting the culture with antibody-bearing magnetic beads.

9. The process of claim 1, wherein the T cell receptor gene is isolated from a tumor specific human cytotoxic T cell clone.

* * * * *